United States Patent [19]

Russell

[11] 3,932,513

[45] Jan. 13, 1976

[54] CYCLOHEXANE OXIDATION

[75] Inventor: Joseph L. Russell, Ridgewood, N.J.

[73] Assignee: Halcon International, Inc., New York, N.Y.

[22] Filed: Feb. 22, 1973

[21] Appl. No.: 334,822

Related U.S. Application Data

[63] Continuation of Ser. No. 113,081, Feb. 5, 1971, abandoned, which is a continuation of Ser. No. 650,996, July 3, 1967, abandoned.

[52] U.S. Cl.... 260/586 AB; 260/586 P; 260/631 R; 260/631 B
[51] Int. Cl.² .................. C07C 27/12; C07C 29/00; C07C 45/02
[58] Field of Search......... 260/586 B, 631 B, 631 R, 260/586 AB, 586 P

[56] References Cited

UNITED STATES PATENTS

| | | | |
|---|---|---|---|
| 3,459,805 | 8/1969 | Russell | 260/586 B |
| 3,488,740 | 1/1970 | Russell | 260/586 B |
| 3,558,687 | 1/1971 | Russell | 260/586 B |

*Primary Examiner*—Norman P. Morgenstern
*Attorney, Agent, or Firm*—William C. Long; David Dick; Riggs T. Stewart

[57] ABSTRACT

The present invention relates to the oxidation of cyclohexane with molecular oxygen in a series of reaction zones, with vaporization of cyclohexane from the last reactor effluent and parallel distribution of this cyclohexane vapor among the series of reaction zones.

4 Claims, 1 Drawing Figure

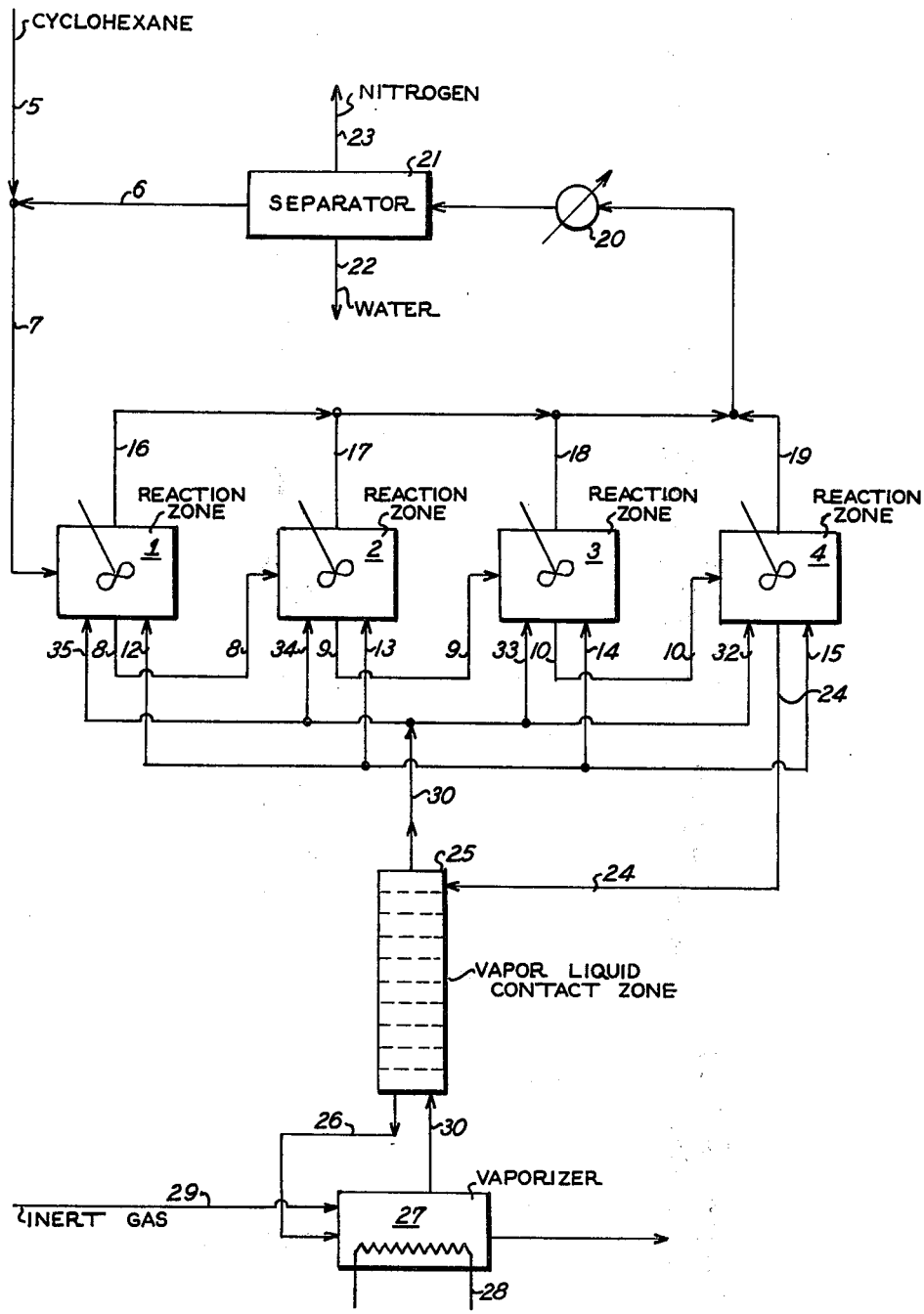

CYCLOHEXANE OXIDATION

This is a continuation, of application Ser. No. 113,081 filed Feb. 5, 1971, which is a continuation of Appln. Ser. No. 650,996, filed July 3, 1967 all now abandoned.

BACKGROUND OF THE INVENTION

The oxidation of cyclohexane is a process of very great commercial importance. The major important oxidation products, cyclohexanol and cyclohexanone, are useful in the production of many high volume chemicals of commerce. For example, such important chemicals as adipic acid, caprotactam, phenol and others are produced from the above oxidation products.

In high volume, efficient processes, it is advantageous that the reaction be carried out in a continuous fashion in a series of separate reaction zones. The reaction selectivities which are achieved by known oxidation procedures, and the methods and equipment employed have not always proved completely satisfactory. For example, the art such as represented by British Pat. No. 1,025,752, has suggested a reaction system whereby vapor from the final reaction mixture is passed in countercurrent flow to the liquid oxidation reaction mixture in the series of reaction zones. Such a procedure has certain disadvantages which include, for example, necessary pressure differentials at various points in the system as well as the enlarged equipment necessary at each point to handle the high vapor flows.

The procedures which have been used in the prior art have not been entirely satisfactory and there has remained considerable room for significant improvements.

SUMMARY OF THE INVENTION

Now, in accordance with the present invention, there is provided an improved method for accomplishing the continuous liquid phase oxidation of cyclohexane in a series of reaction zones. In accordance with the invention, the reaction mixture from the last of the series of zones comprising mainly cyclohexane together with a minor proportion of reaction products is subjected to a vaporization and cyclohexane vapors from this vaporization are then distributed in parallel among the various oxidation zones. By means of this procedure, very significant improvements in oxidation selectively are achieved while at the same time conditions in the entire system tend to be stabilized and the equipment requirements are minimized.

Attached to the instant specification is a drawing which illustrates a suitable method for carrying out the present invention.

DESCRIPTION OF PREFERRED EMBODIMENT

Referring to the accompanying drawing, zones 1, 2, 3 and 4 represent a series of agitated reaction zones suitable for carrying out the liquid phase oxidation of cyclohexane. Each of the zones is equipped with agitating means as well as various vapor and liquid inlet and outlet conduits.

Net fresh cyclohexance is fed through line 8 and is combined with recycle cyclohexane from line 6 and the combined mixture is fed through line 7 into reaction zone 1. After appropriate oxidation in zone 1, liquid reaction mixture is continuously removed by means of line 8 and fed to zone 2. From the zone 2 liquid reaction mixture is removed by means of line 9 and fed to zone 3, with liquid from zone 3 being removed via line 10 and fed to zone 4. The oxidation is carried out in a continuous fashion with the appropriate flows a being requlated in accordance with standard procedures for accomplishing as nearly as possible steady state operation.

Oxygen containing gas, most suitably air, is introduced into the system by means of line 11 and is distributed among the oxidation zones respectively through lines 12, 13, 14 and 15 to accomplish the desired oxidation in each zone. The conditions are selected during the oxidation so as to provide for substantially complete conversion of oxygen in each oxidation zone.

Vapors are removed from each reaction zone respectively through lines 16, 17, 18 and 19. These vapors comprise cyclohexane, water, very small amounts of oxygen and inert gas, usually nitrogen. As shown, the vapors are condensed in condenser 20 and separated in separator 21. Water is discarded by means of line 22 and the non-condensed gases are removed by means of line 23. Condensed cyclohexane is returned to the oxidation system by means of lines 6 and 7.

The reaction mixture from the last oxidation zone 4 comprising mainly unreacted cyclohexane together with a minor proportion of reaction products is removed from zone 4 by means of line 24 and is passed to vapor liquid contact zone 25. Zone 25 can be a bubble cap tray column or any other equivalent vapor liquid contact apparatus. The liquid reaction mixture flows downwardly through zone 25 and is removed through line 26 and passed to vaporizer 27. In vaporizer 27, the reaction mixture is heated and a portion of the contained cyclohexane is vaporized. As shown in the drawing, steam coil 28 is provided to accomplish the heating although it will be apparent that any equivalent means can be employed.

In an especially preferred embodiment of the invention, wherein an inert gas recycle is provided, inert gas is introduced into the vaporizer by means of line 29. Most suitable, this inert gas is a portion of the nitrogen which was separated from separator 21 by means of line 23. However, the inert gas can be from some other zones. Vapors from the vaporizer pass via line 30 to the bottom of vapor liquid contact zone 25. The vapors countercurrently contact the reaction mixture in zone 25 and as a result of this contact such of the reaction products as is contained in the vapors from vaporizer 27 are absorbed in the liquid reaction mixture.

Vapors exiting from zone 25 are removed via line 31 and are passed to the various oxidation zones, vapor passing to zone 4 by means of lines 32, to zone 3 by means of line 33, to zone 2 by means of line 34 and to zone 1 by means of line 35. The amount of vapor distributed to each zone is sufficient to maintain the desired reaction conditions in the particular zone. Generally, a significantly greater amount of vapors is passed to the first oxidation zone, zone 1, because of the somewhat greater heat load in this zone.

Through practice of the present invention, it is possible to carry out the oxidation in each oxidation zone at conditions of very high dilution of oxidation products. This is conductive to achieving the very best selectivities in the oxidation. Additionally, the provision of parallel vapor distribution to the various oxidation zones provides for the greatest process flexibility. The conditions in each zone necessary for optimum operation can most conveniently be set and maintained by the process of this invention. The amount of cyclohexane vapor with or without inert gas in admixture is conveniently regulated to maintain the particular conditions in each zone. For example, the reaction temperature may be the same or may be different for the various zones and is conveniently adjusted by appropriate regulation of the cyclohexane vapor introduced. Likewise, the boilup in each zone can be similarly regulated. Still further, because of the parallel vapor distribution, the size of each oxidation zone and the vapor conduits associated with each zone can be very greatly lessened as compared with systems which involve total vapor passage to each zone.

The oxidation reaction itself is carried out in accordance with conditions and procedures which are well known in the art. The cyclohexane oxidation is carried out in the liquid phase and the conventional heavy metal oxidation catalysts, for example, cobalt naphthenate, can be employed as desired. However, the system of the present invention is particularly applicable where the oxidation reaction is carried out in the presence of a boron adjuvant such as meta boric acid or similar type compounds. For teaching of the details of this type reaction, reference is made to the prior art as illustrated specifically by U. S. Pat. No. 3,243,449. In practice of the invention wherein the boron adjuvant is employed, this material is added entirely to the first reaction zone or alternatively the boron material can be distributed by parallel addition to the oxidation zones.

Temperature which are employed in the present invention are suitably in the range of about 100° to 180°C., and preferably about 140° to 180°C. Oxidation pressures are suitably sufficient to maintain the liquid phase at the elevated reaction temperature while maintaining the necessary conditions of cyclohexane vaporization to insure proper reaction selectivity. An illustrative range is 100 to 500 psig.

Overall conversions are as taught in the prior art. Usually up to about 20% of the cyclohexane can be converted per pass with conversions in the range of 1 to 10% being preferred.

As an additional aspect of the present invention, it is greatly to be desired that the oxygen containing gas introduced into each zone is sparged into the zone separate from the returned cyclohexane vapors. Conventional vapor sparging means can be employed but it is important for successful practice that the oxygen not be combined with the cyclohexane recycle vapor prior to introduction into the body of the reaction liquid in each zone. In the drawing these vapors are depicted as being introduced separately into each oxidation zone and this procedure is of considerable importance for successful practice of the invention in order to avoid explosive and/or non-selective preoxidation of the cyclohexane.

The invention is further illustrated by the following example:

EXAMPLE

Cyclohexane is oxidized as described in the figure accompanying the present specification.

About 1340 mols per hour of fresh cyclohexane is fed in line 5 and combined with about 59,730 mols per hour recycle cyclohexane (containing a small amount of oxygenated materials) and about 900 mols per hour meta boric acid slurried therein, introduced via line 6.

The combined stream at 160°C. is fed to reactor 1 via line 7.

Reactor 1 is maintained with a liquid reaction mixture temperature of 166°C. The reaction pressure on all the oxidation zones is 146 psia. To each oxidation zone respectively through lines 12, 13, 14 and 15 is fed 280 mols per hour oxygen and 1070 mols per hour nntrogen. Substantially complete conversion of the oxygen is achieved in each oxidation zone.

Into zone 1 is sparged via line 35 about 16060 mols per hour cyclohexane (containing a small amount of oxygenated materials) and 3200 mols per hour inerts (mainly nitrogen) at about 174°C. Liquid effluent is removed from zone 1 via line 8 and passed to zone 2 at the rate of about 62000 mols per hour, of which about 635 mols are oxygenated products. Vapor effluent comprising per hour about 15100 mols of cyclohexane, about 30 mols organic oxygenated materials, and about 4610 mols inerts (including water) is removed from zone 1 via line 16.

Oxidation zone 2 is also maintained at a liquid reaction mixture temperature of 166°C. Via line 34 there is introduced into zone 2 about 4280 mols per hour of cyclohexane (containing a small amount of oxygenated materials) and 860 mols per hour of inerts (mainly nitrogen). These vapors are at 174°C. Also introduced into zone 2 by means which are not shown are 130 mols of inerts which have bypassed vaporizer 27. Liquid effluent is removed from zone 2 via line 9 and passed to zone 3 at the rate of about 58100 mols per hour, of which about 973 mols are oxygenated products. Vapor effluent comprising per hour about 8154 mols cyclohexane, 26 mols organic oxygenated materials, and about 2400 mols inerts (including water) is removed from zone 2 via line 17.

Oxidation zone 3 is maintained at a reaction liquid temperature of 167°C. Into zone 3 there is introduced per hour via line 33 about 4280 mols cyclohexane and 860 mols per hour inerts (mainly nitrogen) at 174°C. Also, by means not shown, there is introduced into zone 3 about 200 mols per hour of recycle inert gas which has bypassed vaporizer 27. Liquid effluent is removed from zone 3 via line 10 in amount of 53300 mols per hour of which about 1298 mols are oxygenated products and fed to zone 4. Vapor effluent comprising 9042 mols per hour cyclohexane, 38 mols per hour organic oxygenated materials and 2470 mols per hour (inerts per hour) are removed from zone 3 via line 18.

Oxidation zone 4 is maintained at a liquid reaction temperature of 168°C. Into zone 4 via line 32 is introduced 4280 mols per hour cyclohexane and 860 mols per hour of inerts (mainly nitrogen) at 174°C. Also introduced by means not shown is 260 mols per hour recycle inerts which have bypassed vaporizer 27. Vapor effluent is removed via line 19 comprising 9528 mols per hour cyclohexane, 52 mols per hour oxygenated organic materials and 2530 mols per hour inerts (including water). A liquid effluent is amount of 48000 mols per hour containing 1608 mols oxidation products is removed by means of line 24 and passed to the top of vapor liquid contact zone 25.

The combined vapors from each of the oxidation zones are cooled in heat exchange zone 20 in order to condense the condensible materials. The cooled mixture passes to separation zone 21 with water being separated via line 22 and inerts via line 23. A suitable quantity of the inerts is recycled via line 29 to vaporizer 27 with another portion passing directly to reactors 2, 3 and 4 as above indicated. Liquid cyclohexane is removed via line 6 and recycled to the oxidation zone 1 as indicated after appropriate combination with meta boric acid (not shown).

Liquid reaction mixture from vapor liquid contact zone 25 passes via line 26 to vaporizer 27 wherein the mixture is heated by means of steam coil 28. Inert gas is introduced to the vaporizer via line 29. The combined vapors are passed via line 30 through zone 25 and thence via line 31 to the various oxidation zones as above indicated.

From the liquid effluent from vaporizer 27 there are recovered by hydrolysis and other known procedures a cyclohexane oxidation reaction mixture with a molecular yield of cyclohexanol and cyclohexanone of 86.9%. Recovered unreacted cyclohexane is recycled to line 6 by means not shown.

By way of contrast, when prior procedures are employed wherein the recycle cyclohexane in line 6 is vaporized and distributed among the reactors, oxidation selectivities of the order of 80.6 are achieved.

Further, where systems are employed using countercurrent flow of cyclohexane vapors, the volumes of the corresponding reactors are increased severalfold thus imposing severe economic penalty as contrasted with the practice of the present invention. For example, in the accompanying drawing, if all of the vapors in line 31 were passed countercurrent to the liquid in the reactors, as suggested in the prior art, the area and volume of reactors would be increased by a factor of about four compared to that needed when using this invention. Furthermore, the larger reactor sizes necessitates much longer liquid residence times in the oxidation zone. It is well known that long residence times result in substantial degradation of the desired oxidation products.

I claim:

1. The process of oxidizing cyclohexane which comprises
    contacting cyclohexane in the liquid phase at a temperature of from about 100° to 180°C with a molecular-oxygen containing gas in each of a series of separate and inter-connected oxidation zones,
    passing the liquid effluent from one zone to the next zone in series,
    removing vapors from each oxidation zone respectively,
    condensing said vapors to form a hydrocarbon phase and an aqueous phase,
    separating said aqueous phase from said hydrocarbon phase,
    returning the hydrocarbon phase in liquid form to the first of the series of oxidation zones,
    removing a liquid effluent mainly containing unreacted cyclohexane and also containing oxidation products from the last of the series of oxidation zones,
    subjecting said liquid effluent from said last zone to vaporization of contained cyclohexane prior to recovery of the oxidation product, and
    returning directly to each of said oxidation zones a portion of said vaporized cyclohexane while in vaporized form.

2. The process of oxidizing cyclohexane which comprises
    contacting cyclohexane in the liquid phase at a temperature of from about 100° to about 180°C with a molecular-oxygen containing gas in the presence of a boron oxidation adjuvant compound in each of a series of separate and inter-connected oxidation zones,
    passing the liquid effluent from one zone to the next zone in series,
    removing vapors from each oxidation zone respectively,
    condensing said vapors to form a hydrocarbon phase and an aqueous phase,
    separating said aqueous phase from said hydrocarbon phase,
    returning the hydrocarbon phase in liquid form to the first of the series of oxidation zones,
    removing a liquid effluent mainly containing unreacted cyclohexane and also containing oxidation products from the last of the series of oxidation zones,
    subjecting said liquid effluent from said last zone to vaporization of contained cyclohexane prior to recovery of the oxidation product, and
    returning directly to each of said oxidation zones a portion of said vaporized cyclohexane while in vaporized form.

3. The method of claim 2 wherein the process further comprises recycling of an inert gas and at least a portion of the inert gas is combined with the cyclohexane vapors returned in parallel to the oxidation zones.

4. the method of claim 2 wherein the oxygen containing gas necessary for the oxidation is sparged into each oxidation zone separately from the returned cyclohexane vapor.

* * * * *